United States Patent [19]
Kikuchi et al.

[11] Patent Number: 5,932,453
[45] Date of Patent: Aug. 3, 1999

[54] PROCESS FOR PRODUCING L-AMINO ACID THROUGH FERMENTATION

[75] Inventors: Yoshimi Kikuchi; Kazuo Nakanishi; Hiroyuki Kojima, all of Kawasaki, Japan

[73] Assignee: Ajinomoto Co., Ltd., Tokyo, Japan

[21] Appl. No.: 08/950,737

[22] Filed: Oct. 15, 1997

[30] Foreign Application Priority Data

Oct. 15, 1996 [JP] Japan .................................. 8-272114

[51] Int. Cl.$^6$ ........................... C12N 15/09; C12N 15/54; C12N 15/63
[52] U.S. Cl. ................... 435/115; 435/194; 435/252.33; 435/320.1; 435/172.1; 536/23.2
[58] Field of Search ..................... 435/115, 194, 435/252.33, 320.1, 172.1; 536/23.2

[56] References Cited

U.S. PATENT DOCUMENTS

| | | | |
|---|---|---|---|
| 5,243,039 | 9/1993 | Schendel et al. | 536/23.2 |
| 5,367,110 | 11/1994 | Galili et al. | 800/205 |
| 5,661,012 | 8/1997 | Sano et al. | 435/115 |

FOREIGN PATENT DOCUMENTS

| | | |
|---|---|---|
| Wo 94/11517 | 5/1994 | Japan . |
| WO 95/16042 | 6/1995 | Japan . |
| WO 96/41871 | 12/1996 | Japan . |
| WO 93/19190 | 9/1993 | U.S. . |
| WO 95/15392 | 6/1995 | U.S. . |
| WO 95/31554 | 11/1995 | U.S. . |

OTHER PUBLICATIONS

Cassan et al. Nucleotide sequence of lysC gene encoding the lysine–sensitive aspartokinase III of Escherichia coli K12. J. Biol. Chem. 261(3) : 1052–1057 (1986).

*Primary Examiner*—Keith D. Hendricks
*Assistant Examiner*—Bradley S. Mayhew
*Attorney, Agent, or Firm*—Oblon, Spivak, McClelland, Maier & Neustadt, P.C.

[57] ABSTRACT

A DNA encoding aspartokinase III derived from bacteria of the genus Escherichia and having mutation by which feedback inhibition with L-lysine is released is introduced into cells to form transformant bacteria of the genus Escherichia. These bacteria are incubated in an appropriate culture medium. An L-amino acid is produced and accumulated in the culture, and collected from this culture.

79 Claims, 3 Drawing Sheets

PROCESS FOR PRODUCING L-AMINO ACID THROUGH FERMENTATION

BACKGROUND OF THE INVENTION

1. Field of the Invention

The present invention is concerned with a microorganism. More specifically, the present invention relates to a process for producing an L-amino acid through fermentation, and a DNA and a microorganism which are used in this process.

2. Description of Related Art

When L-lysine is produced through fermentation, strains separated from the natural field or synthetic strains thereof are used to improve the productivity. A large number of L-lysine-productive synthetic mutants are known, and many of them are aminoethylcysteine (AEC)-resistant mutants belonging to the genus Brevibacterium, Corynebacterium, Bacillus or Escherichia. Further, transformants obtained upon using recombinant DNAs are also employed (U.S. Pat. No. 4,278,765). Thus, a variety of technologies for increasing the productivity of amino acids are disclosed.

For example, with respect to the genus Escherichia, a process for producing L-lysine by enhancing a dihydrodipicolinic acid synthetase (hereinafter abbreviated at times as "DDPS") is described in Japanese Laid-Open (Kokai) No. 18,596/1981, U.S. Pat. No. 4,346,170 and Applied Microbiology and Biotechnology 15, 227 (1982).

The dihydrodipicolinic acid synthetase (DDPS) is an enzyme that catalyzes dehydro-condensation of aspartosemialdehyde and pyruvic acid to form dihydrodipicolinic acid. This release feedback inhibition with lysine is disclosed in International Laid-Open Pamphlet WO95/16042.

When L-threonine is produced through fermentation, strains separated from the natural field or synthetic mutants thereof are used as microorganisms. A large number of L-threonine-productive synthetic mutants have been known, and many of them are resistant to α-amino-β-hydroxyvaleric acid, belonging to the genus Escherichia, Serratia, Brevibacterium or Corynebacterium. With respect to the genus Escherichia, a process for producing L-threonine using a strain transformed with a recombinant plasmid containing a threonine operon is described in Japanese Laid-Open (Kokai) Nos. 131,397/1980, 31,691/1984 and 15,696/1981 and Japanese Patent Announcement No. 501,682/1991.

Further, a process for producing L-threonine using *E. coli* containing lysC that has mutation by which to release feedback inhibition with lysine is disclosed in International Laid-Open Pamphlet WO94/11517.

SUMMARY OF THE INVENTION

The present invention aims to obtain AKIII derived from bacteria of the genus Escherichia in which the feedback inhibition with L-lysine is released well, and to provide a process for producing an L-amino acid through fermentation, which is more improved than before.

The present inventors have assiduously conducted investigations to solve the above-mentioned problems, and have consequently succeeded in obtaining a DNA encoding AKII derived from bacteria of the genus Escherichia in which the feedback inhibition with L-lysine is released well. A DNA encoding AKIII derived from bacteria of the genus Escherichia in reaction is an entry for an L-lysine biosynthesis system in the biosynthesis of an aspartic acid-type amino acid. This enzyme is known to serve as an important regulatory site of the L-lysine biosynthesis in bacteria of the genus Escherichia along with aspartokinase.

DDPS is encoded in a gene called dapA in *Escherichia coli* (*E. coli*). This dapA has been already cloned, and its base sequence has been determined [Richaud, F. et al., J. Bacteriol. 297 (1986)].

Meanwhile, aspartokinase (hereinafter abbreviated at times as "AK") is an enzyme that catalyzes a reaction of converting aspartic acid into β-phosphoaspartic acid, and is a main regulatory enzyme in the biosynthesis system of an aspartic acid-type amino acid. AK of *E. coli* includes three types (AKI, AKII, AKIII), and two of these are conjugated enzymes with homoserine dehydrogenase (hereinafter abbreviated at times as "HD"). One of these conjugated enzymes is AKI-HDI encoded in thrA gene, and the other is AKII-HDII encoded in metLM gene. AKI undergoes concerted suppression with threonine and isoleucine and inhibition with threonine, and AKII undergoes suppression with methionine.

Meanwhile, AKIII alone is an enzyme of a single function, and it is a product of a gene called lysC. It is known to undergo suppression and feedback inhibition with L-lysine. The ratio of activities thereof in cells is AKI:AKII:AKIII=approximately 5:1:4.

This lysC of *E. coli* has been already cloned and its base sequence has been determined [Cassan, M., Parsot, C., Cohen, G. N., and Patte, J. C., J. Biol. Chem. 261, 1052 (1986)].

A process for producing L-lysine using *E. coli* containing dapA that has mutation by which to release feedback inhibition with lysine and lysC that has mutation by which to which the feedback inhibition with L-lysine is released well is called at times mutant lysC gene or mutant AKIII gene in the present specification.

A DNA encoding DDPS derived from *E. coli* in which the feedback inhibition with L-lysine is released well is called at times mutant dapA gene or mutant DDPS gene in the present specification.

Further, the present inventors have produced bacteria of the genus Escherichia containing mutant lysC in cells, and they have found that a considerable amount of L-lysine or L-threonine can be produced and accumulated in the culture.

That is, the present invention relates to a DNA encoding aspartokinase III of bacteria belonging to the genus Escherichia and having in the encoding region mutation by which to release feedback inhibition with lysine of said aspartokinase III, said mutation being mutation by which the 318th methionine residue of aspartokinase III is substituted with another amino acid residue and the 323rd glycine residue with another amino acid residue, mutation by which the 325th leucine residue is substituted with another amino acid and the 347th valine residue with another amino acid residue, mutation by which the 323rd glycine residue is substituted with another amino acid residue and the 347th valine residue with another amino acid residue, mutation by which the 325th leucine residue is substituted with another amino acid residue and the 345th serine residue with another amino acid residue, mutation by which the 323rd glycine residue is substituted with another amino acid residue and the 358th serine residue with another amino acid residue, mutation by which the 344th threonine residue is substituted with another amino acid residue, mutation by which the 250th glutamic acid residue is substituted with another amino acid residue, mutation by which the 346th glutamic acid residue is substituted with another amino acid residue and the 347th leucine residue with another amino acid residue, mutation by which the 250th glutamic acid residue is substituted with another amino acid residue and the 364th threonine residue with another amino acid residue, mutation by which the 202nd aspartic acid residue is substituted with another amino acid residue and the 321st serine residue with another amino acid residue, mutation by which the 283rd arginine residue is substituted with another amino acid residue, the 333rd alanine residue with another amino acid residue, the 338th serine residue with another amino acid residue, the 346th glutamic acid residue with another amino acid residue and the 414th asparagine residue with another amino acid residue, or mutation by which the 318th methionine residue is substituted with another amino acid residue, the 321st serine residue with another amino acid residue, the 328th valine residue with another amino acid residue, the 349th valine residue with another amino acid residue and the 405th glutamic acid residue with another amino acid residue.

Preferably, the present invention relates to a DNA encoding aspartokinase III of bacteria belonging to the genus Escherichia and having in the encoding region mutation by which to release feedback inhibition with lysine of said aspartokinase III, said mutation being mutation by which the 318th methionine residue of aspartokinase III is substituted with an isoleucine residue and the 323rd glycine residue with an aspartic acid residue, mutation by which the 325th leucine residue is substituted with a phenylalanine residue and the 347th valine residue with a methionine residue, mutation by which the 323rd glycine residue is substituted with an aspartic acid residue and the 347th valine residue with a methionine residue, mutation by which the 325th leucine residue is substituted with a phenylalanine residue and the 345th serine residue with a leucine residue, mutation by which the 323rd glycine residue is substituted with an aspartic acid residue and the 358th serine residue with a leucine residue, mutation by which the 344th threonine residue is substituted with a methionine residue, mutation by which the 250th glutamic acid residue is substituted with a lysine residue, mutation by which the 346th glutamic acid residue is substituted with a lysine residue and the 347th leucine residue with a phenylalanine residue, mutation by which the 250th glutamic acid residue is substituted with a lysine residue and the 364th threonine residue with a methionine residue, mutation by which the 202nd aspartic acid residue is substituted with a glycine residue and the 321st serine residue with a proline residue, mutation by which the 283rd arginine residue is substituted with a serine residue, the 333rd alanine residue with a threonine residue, the 338th serine residue with a threonine residue, the 346th glutamic acid residue with an aspartic acid residue and the 414th asparagine residue with a serine residue, or mutation by which the 318th methionine residue is substituted with a lysine residue, the 321st serine residue with a proline residue, the 328th valine residue with a phenylalanine residue, the 349th valine residue with a glycine residue and the 405th glutamic acid residue with a valine residue.

The present invention relates to the above-mentioned recombinant DNA which is produced by ligating the above DNA with a vector DNA capable of autonomic replication in cells of bacteria of the genus Escherichia, as well as to a microorganism of the genus Escherichia having this DNA.

The present invention relates to a process for producing an L-amino acid, which comprises incubating the above-mentioned microorganism having an ability of producing an L-amino acid in a fermentation medium, producing and accumulating an L-amino acid in the culture, and collecting the L-amino acid from the culture.

In the present specification, a DNA encoding DDPS or AKIII or a DNA containing the same and a promoter is called at times "DDPS gene" or "AKIII gene". Further, a mutant enzyme in which the feedback inhibition with L-lysine is released is called at times simply "a mutant enzyme", and a DNA encoding the same or a DNA containing the same and a promoter as "a mutant gene". Still further, "to release the feedback inhibition with L-lysine" means that the inhibition is substantially released, and it is not necessarily released completely.

The present invention is described in detail below.

(1) DNA encoding mutant aspartokinase (AKIII) of present invention.

The DNA encoding mutant aspartokinase (AKIII) of the present invention is a DNA encoding wild-type AKIII that has mutation by which to release feedback inhibition with L-lysine of AKIII to be encoded. As AKIII, AKIII derived from bacteria of the genus Escherichia, especially AKIII derived from E. coli is mentioned. The mutation by which to release the feedback inhibition with L-lysine of AKIII includes, in the amino acid sequence of AKIII represented by SEQ ID NO:2, as counted from the N-terminus of AKIII, (a) mutation by which the 318th methionine residue of aspartokinase III is substituted with another amino acid residue, preferably with an isoleucine residue and the 323rd glycine residue with another amino acid residue, preferably with an aspartic acid residue, (b) mutation by which the 325th leucine residue is substituted with another amino acid, preferably with a phenylalanine residue, and the 347th valine residue with another amino acid residue, preferably with a methionine residue, (c) mutation by which the 323rd glycine residue is substituted with another amino acid residue, preferably with an aspartic acid residue, and the 347th valine residue with another amino acid residue, preferably with a methionine residue, (d) mutation by which the 325th leucine residue is substituted with another amino acid residue, preferably with a phenylalanine residue, and the 345th serine residue with another amino acid residue, preferably with a leucine residue, (e) mutation by which the 323rd glycine residue is substituted with another amino acid residue, preferably with an aspartic acid residue, and the 358th serine residue with another amino acid residue, preferably with a leucine residue, (f) mutation by which the 344th threonine residue is substituted with another amino acid residue, preferably with a methionine residue, (g) mutation by which the 250th glutamic acid residue is substituted with another amino acid residue, preferably with a lysine residue, (h) mutation by which the 346th glutamic acid residue is substituted with another amino acid residue, preferably with a lysine residue, and the 347th leucine residue with another amino acid residue, preferably with a phenylalanine residue, (i) mutation by which the 250th glutamic acid residue is substituted with another amino acid residue, preferably with a lysine residue, and the 364th threonine residue with another amino acid residue, preferably with a methionine residue, (j) mutation by which the 202nd aspartic acid residue is substituted with another amino acid residue, preferably with a glycine residue, and the 321st serine residue with another amino acid residue, preferably with a proline residue, (k) mutation by which the 283rd arginine residue is substituted with another amino acid residue, preferably with a serine residue, the 333rd alanine residue with another amino acid residue, preferably with a threonine residue, the 338th serine residue with another amino acid residue, preferably with a threonine residue, the 346th glutamic acid residue with another amino acid residue, preferably with an aspartic acid residue, and the 414th asparagine residue with another amino acid residue, preferably with a serine residue, or (l) mutation by which the 318th methionine residue is substituted with another amino acid residue, preferably with a lysine residue, the 321st serine residue with another amino acid residue, preferably with a proline residue, the 328th valine residue with another amino acid residue, preferably with a phenylalanine residue, the 349th valine residue with another amino acid residue, preferably with a glycine residue, and the 405th glutamic acid residue with another amino acid residue, preferably with a valine residue.

The DNA encoding wild-type AKIII is not particularly limited. A DNA encoding AKIII derived genus Escherichia, for example, *E. coli* is mentioned. Specifically, a DNA encoding the amino acid sequence, wherein the amino acid sequence is represented by SEQ ID NO:2, and further the sequence represented by Base Nos. 584 to 1930 in the base sequence represented by SEQ ID NO:1 are mentioned. AKIII of *E. coli* is encoded in lysC gene.

Of the above-mentioned sequences, the sequence having the mutation of the base sequence by which to cause the substitution of the amino acid residue is the DNA encoding mutant AKIII of the present invention. A type of a codon corresponding to the amino acid residue substituted is not particularly limited so long as it encodes that amino acid residue. The amino acid sequence of wild-type AKIII varies slightly depending on the bacteria or strains. The sequence having substitution, deletion or insertion of the amino acid residue in the position which does not participate in the enzymatic activity is also included in mutant AKIII gene of the present invention.

For example, the base sequence (SEQ ID NO:1) of wild-type lysC gene obtained in Example 1 is different from the base sequence of lysC of *E. coli* K-12 JC411 strain which has been already made public [Cassan, M., Parsot. C., Cohen, G. N., and Patte, J. C., J. Biol. Chem. 261, 1052 (1986)] by 6 sites. The amino acid residues to be encoded are different in 2 sites among 6 sites (in lysC of JC411 strain, the 58th glycine residue, as counted from the N-terminus, is substituted with a cysteine residue and the 401st glycine residue with an alanine residue in the amino acid sequence of lysC represented by SEQ ID NO:2. If any of the above-mentioned mutations a) to 1) is introduced into lysC having the same sequence of lysC of *E. coli* K-12 JC411 strain, it is expected to obtain lysC having mutation by which feedback inhibition with L-lysine is released.

The DNA encoding mutant AKIII in which the feedback inhibition with lysine is released is obtained as follows. First, a DNA containing wild-type AKIII gene or AKIII gene having another mutation is mutagenized in vitro, and the DNA mutagenized is ligated with a vector DNA adaptable to a host to form a recombinant DNA. The recombinant DNA is introduced into a host microorganism to obtain a transformant. When the transformant that comes to express mutant AKIII is selected, this transformant retains the mutant gene. Further, a DNA containing wild-type AKIII gene or AKIII gene having another mutation is ligated with a vector DNA adaptable to a host to form a recombinant DNA. The recombinant DNA is then mutagenized in vitro, and the DNA mutagenized is introduced into a host microorganisms to obtain a transformant. When the transformant that comes to express mutant AKIII is selected, this transformant also retains the mutant gene. Alternatively, it is also possible that a microorganism producing a wild-type enzyme is mutagenized to form a mutant strain producing a mutant enzyme, and a mutant gene is then obtained from this mutant strain.

As an agent for directly mutagenizing a DNA, hydroxylamine or the like is mentioned. Hydroxylamine is a chemical mutagenization agent that causes mutagenization from cytosine into thymine by changing cytosine to $N^4$-hydroxycytosine. Further, when a microorganism is itself mutagenized, irradiation with ultraviolet light or treatment with a mutagenization agent ordinarily used in artificial mutation, such as N-methyl-N'-nitro-N-nitrosoguanidine (NTG) is conducted.

As donor bacteria of the DNA containing wild-type AKIII gene or AKIII gene having another mutation, any microorganisms belonging to the genus Escherichia can be used. Specifically, those described in documents of F. C. Neidhardt et al. (Neidhardt, F. C. et al., *Escherichia coli* and *Salmonella typhimurium*, American Society for Microbiology, Washington D.C., p. 1208, Table 1) are available. Examples thereof are *E. coli* JM109 strain and *E. Coli* MC1061 strain.

Figure 1:
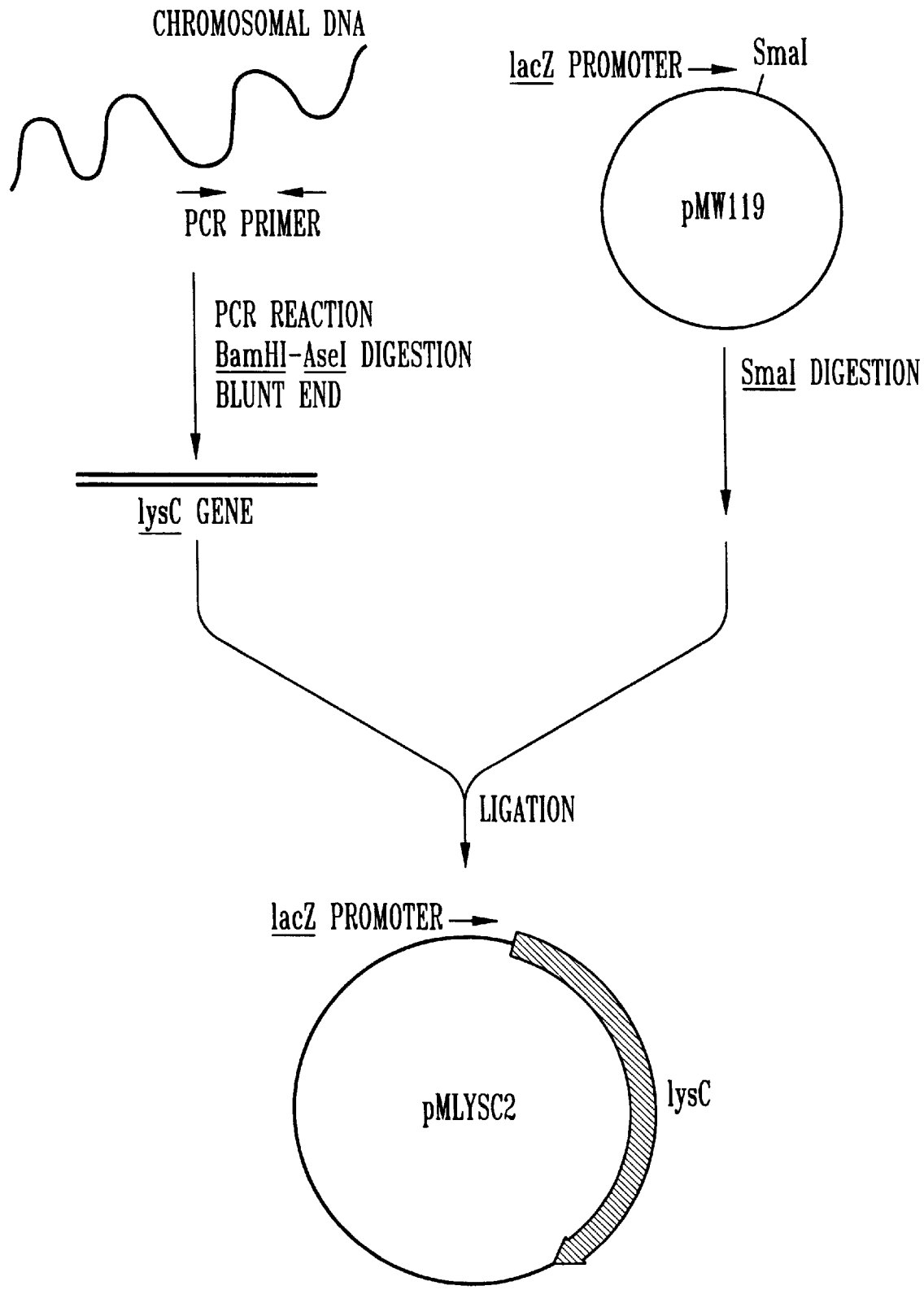
FIG. 1 illustrates the preparation process for pMLYSC2.

DESCRIPTION OF THE PREFERRED EMBODIMENTS (1) Procurement of wild-type AKIII gene.

An example of producing a DNA containing AKIII gene is described below. First, for example, wild-type *E. coli* MC1061 strain having lysC is incubated to obtain a culture. The above-mentioned microorganism may be incubated through usual solid culture. In view of an efficiency of cell collection, it is preferable to employ liquid culture. In this case, the culture medium is, for example, one obtained by adding one or more types of inorganic salts selected from potassium monohydrogen phosphate, potassium dihydrogen phosphate, magnesium sulfate, sodium chloride, magnesium chloride, ferrous chloride, ferrous sulfate and manganese sulfate to one or more carbon sources selected from yeast extract, peptone, meat extract, corn steep liquor and a soybean or wheat effluent, and further adding thereto suitable amounts of a saccharine starting material, vitamin and the like as required. It is suitable to adjust the initial pH of the culture medium to between 6 and 8. The incubation is conducted at from 30 to 42° C., preferably at approximately 37° C. for from 4 to 24 hours through submerged-aerial stirring culture, shaking culture or stationary culture.

The thus-obtained culture is separated, for example, at 3,000 rpm for 5 minutes to obtain E. Coli MC1061 strain. A chromosomal DNA can be obtained from this strain by, for example, the method of Saito and Miura [Biochem. Biophys. Acta. 72, 619, (1963)] or the method of K. S. Kirby [Biochem. J. 64, 405, (1956)].

In order to isolate AKIII gene from the resulting chromosomal DNA, the chromosomal DNA library is prepared. First, the chromosomal DNA is partially cleaved with an appropriate restriction endonuclease to obtain various fragmental mixtures. If the degree of cleavage is controlled by controlling a cleavage time or the like, a wide variety of fragmental mixtures are formed. For example, the chromosomal DNA is reacted with Sau 3AI at an enzyme concentration of from 1 to 10 units/ml at a temperature of 30° C. or higher, preferably at 37° C. for a period of time of from 1 minute to 2 hours to digest the same.

Then, the chromosomal DNA fragment cleaved is ligated with a vector DNA capable of autonomous replication within cells of bacteria of the genus Escherichia to form a recombinant DNA. Specifically, a vector DNA is reacted with a restriction endonuclease that allows formation of the same terminal base sequence as the restriction endonuclease Sau 3AI used in the cleavage of the chromosomal DNA, for example, Bam HI at an enzyme concentration of from 1 to 100 units/min at a temperature of 30° C. or higher for 1 hour or more, preferably for from 1 to 3 hours to completely digest the same, and it is cleaved. Subsequently, the above-obtained chromosomal DNA fragmental mixture is mixed with the vector DNA cleaved. The mixture is reacted with a DNA ligase, preferably with T4 DNA ligase at an enzyme concentration of from 1 to 100 units/min at a temperature of from 4 to 116° C. for 1 hour or more, preferably for from 6 to 24 hours to form a recombinant DNA.

A microorganism of the genus Escherichia, for example, E. coli K-12 strain, preferably a strain wholly deficient in AKI, AKII and AKIII, for example, E. coli GT3 strain [which can be obtained from E. coli Genetic Stock Center (Connecticut, U.S.A.)] is transformed to prepare the chromosomal DNA library. The transformation can be conducted by the method of D. M. Morrison [Methods in Enzymology 68, 326, (1979)] or a method in which permeability of a DNA is increased by treating cells of recipient bacteria with calcium chloride [Mandel, M. and Higa, A., J. Mol. Biol. 53, 159 (1970)].

A strain having a recombinant DNA of AKIII gene is obtained from a strain having an increased AKIII activity or a strain in which auxotrophy caused by the deletion of AKIII gene has been offset in the resulting chromosomal DNA library. For example, when a mutant wholly deficient in AK is used as a host, a recombinant strain which can be grown on a medium free from L-lysine, L-threonine, L-methionine and diaminopimelic acid or a culture medium free from homoserine and diaminopimeric acid, and the recombinant DNA is recovered from this strain, making it possible to obtain a DNA fragment containing AKIII gene. A cell extract is prepared from a candidate strain, and a crude enzyme solution is formed from the cell extract. Then, the AKIII activity is identified. The enzymatic activity of AKIII can be measured by the method of E. R. Stadbman (Stadbman, E. R., Cohen, G. N., LeBras, G., and Robichon-Szulmajster, H., J. Biol. Chem. 236, 2033 (1961)].

A recombinant DNA obtained by inserting the DNA containing AKIII gene into the vector DNA can be isolated by, for example, the method of P. Guerry et al. [J. Bacteriol. 116, 1064, (1973)] or the method of D. B. Clewell [J. Bacteriol. 110, 667, (1972)].

Wild-type AKIII gene is also obtained by preparing a chromosomal DNA from a strain having AKIII gene on a chromosome by the method of Saito and Miura, and amplifying AKIII gene through polymerase chain reaction [PCR, White, T. J. et al, Trends Genet. 5, 185 (1989)]. A DNA primer used in the amplification is one complementary to both 3'-termini of a DNA double strand containing the overall region of AKIII gene or a part thereof. When only a part of the region of AKIII gene is amplified, it is necessary to screen a DNA fragment containing the overall region from the chromosomal DNA library using the DNA fragment having the part of the region of AKIII as a primer. When the whole region of AKIII gene is amplified, the PCR solution containing the DNA fragment having the amplified AKIII gene is subjected to agarose gel electrophoresis, and a desired DNA fragment is then extracted, whereby the DNA fragment containing AKIII gene can be recovered.

The DNA primer can be appropriately formed on the basis of, for example, the known sequence of E. coli [Cassan, M., Parsot, C., Cohen, G. N. and Patte, J. C., J. Biol. Chem. 261, 1052 (1986)]. A primer capable of amplifying a region composed of 1,347 bases encoding lysC gene is appropriate. For example, two types of primers represented by SEQ ID NO:3 and SEQ ID NO:4 are appropriate. A primer DNA can be synthesized by a usual method, for example, a phosphoamidide method [Tetrahedron Letters 22, 1859 (1981)] using a commercially available DNA synthesizer (for example, a DNA synthesizer Model 380B manufactured by Applied Biosystems).

Further, PCR can be conducted by a method indicated by a supplier using a commercially available PCR device (DNA Thermal Cycler Model PJ2000 manufactured by Takara Shuzo Co., Ltd.) and a Taq DNA polymerase (supplied by Takara Shuzo Co., Ltd.).

AKIII gene amplified through PCR is ligated with a vector DNA capable of autonomous replication in cells of bacteria belonging to the genus Escherichia, and introduced into the cells of bacteria of the genus Escherichia, whereby the introduction of mutation into AKIII gene can easily be conducted. The vector DNA, the transformation and the identification of the presence of AKIII gene are the same as those described above.

(2) Introduction of mutation into AKIII gene.

The above-obtained AKIII gene is subjected to mutation such as substitution, insertion or deletion of the amino acid residue by the recombinant PCR method [Higuchi, R. 61, in PCR Technology (Erlich, H. A. Eds., Stockton Press (1989)], a site specific mutation method [Kramer, W. and Frits, H. J., Methods in Enzymology 154, 350 (1987); Kunkel, T. A. et al., Methods in Enzymology 154, 367 (1987)], or the like. These methods can cause the desired mutation in the desired site.

The mutation or the random mutation can be introduced into the desired site by a method of chemically synthesizing a desired gene.

Further, there is a method in which AKIII gene on a chromosome or a plasmid is directly treated with hydroxylamine [Hashimoto, T. and Sekiguchi M., J. Bacteriol. 159, 1039 (1984)]. Still further, a method in which bacteria of the genus Escherichia containing AKIII gene is irradiated with ultraviolet light or a method using a chemical agent such as N-methyl-N'-nitrosoguanidine or nitrous acid may be employed. The mutation can be introduced randomly by these methods.

A method of selecting mutant AKIII gene is described below. That is, first, a recombinant DNA containing AKIII gene mutagenized is transformed into a completely AK-deficient strain, for example, E. coli GT3 strain. Then, the transformant is incubated on a minimal medium, for example, M9, containing a considerable amount of L-lysine. Since sole AK is inhibited with L-lysine in a strain having a recombinant DNA containing wild-type AKIII gene, L-threonine, L-isoleucine, L-methionine and diaminopimerinic acid (DAP) cannot be synthesized, controlling the growth thereof. Meanwhile, a strain having a recombinant DNA mutant AKIII gene in which inhibition with L-lysine is released must be grown on a minimal medium containing a considerable amount of L-lysine. Upon utilizing this phenomenon, it is possible to select a strain resistant to L-lysine or S-2-aminoethylcysteine (AEC) analogous to L-lysine in the growth, namely, a strain having a recombinant DNA containing mutant AKIII gene in which inhibition is released.

The thus-obtained recombinant gene as a recombinant DNA is introduced into a suitable microorganism (host), and expressed to be able to obtain a microorganism containing AKIII in which feedback inhibition is released.

As the host, microorganisms belonging to the genus Escherichia are preferable. For example, *Escherichia coli* (*E. coli*) is mentioned.

Further, a substance obtained by taking out a mutant AKIII gene fragment from a recombinant DNA and inserting the same into the other vector may be used. As the vector DNA which can be used in the present invention, a plasmid vector DNA is preferable. Examples thereof include pUC19, pUC18, pBR322, pHSG299, pHSG298, pHSG399, pHSG398, RSF100, pMW119, pMW118, pMW219 and pMW218. A phage DNA vector and a transposon vector are also available.

In order to efficiently express mutant AKIII gene, another promoter that acts within microorganisms such as lac, trp and PL may be ligated with an upstream region of a DNA encoding mutant AKIII. Or, a promoter contained in AKIII gene is used as such by being amplified.

As mentioned above, the substance obtained by inserting the mutant gene into the vector DNA capable of autonomous replication may be introduced into a host, and retained therein as an extrachromosomal DNA like a plasmid. Or, the mutant gene may be inserted into a chromosome of a host microorganism through transduction, with a transposon (Berg, D. E. and Berg, C. M., Bio/Technol. 1, 417 (1983)], with Mu phage [Japanese Laid-Open (Kokai) No. 109,985/1990] or through complementary recombination [Experiments in Molecular Genetics, Cold Spring Harbor Lab. (1972)].

(3) Production of L-amino acid according to present invention.

An L-amino acid can be produced at good efficiency by incubating in an appropriate culture medium bacteria of the genus Escherichia which have been transformed upon introducing the above-obtained mutant AKIII gene, producing and accumulating an L-amino acid in the culture, and collecting the L-amino acid from the culture.

The bacteria of the genus Escherichia containing AK in which feedback inhibition with L-lysine is released includes bacteria of the genus Escherichia which are transformed by inserting a DNA encoding AKIII having mutation by which to release feedback inhibition with L-lysine into a chromosomal DNA, and bacteria of the genus Escherichia which are transformed by introducing into cells a recombinant DNA formed upon ligating the above-mentioned DNA with a vector DNA capable of autonomous replication in cells of bacteria of the genus Escherichia. Further, mutants of bacteria of the genus Escherichia that allow production of mutant AKIII by mutagenizing cells of bacteria of the genus Escherichia are also available.

With respect to the bacteria of the genus Escherichia which are used as a host for transformation, any bacteria can be used if a promoter of mutant AKIII gene or another promoter for expressing this gene acts within the cells thereof. Or, when mutant AKIII gene is introduced into a plasmid as an extrachromosomal DNA, any bacteria can be used if a replication origin of a vector DNA used for introduction can act within the cells thereof and it can be replicated.

The culture medium used to incubate the microorganism having the mutant gene according to the present invention is a common culture medium containing a carbon source, a nitrogen source, inorganic ions and other organic substances as required.

Examples of the carbon source include saccharides such as glucose, lactose, galactose, fructose and a starch hydrolyzate; alcohols such as glycerol and sorbitol; and organic acids such as fumaric acid, citric acid and succinic acid.

Examples of the carbon source include inorganic ammonium salts such as ammonium sulfate, ammonium chloride and ammonium phosphate; a soybean hydrolyzate; ammonia gas and aqueous ammonia.

As an organic micronutrient source, it is advisable to contain a suitable amount of a requirement substance such as vitamin B or L-isoleucine, or a yeast extract. Further, potassium phosphate, magnesium sulfate, iron ions and manganese ions are added in small amounts as required.

The incubation is conducted aerobically for from 16 to 72 hours. The incubation temperature is between 25° C. and 45° C. The pH is adjusted to between 5 and 8 during the incubation. An inorganic or organic, acidic or alkaline substance and further an ammonia gas can be used to adjust the pH.

An L-amino acid can usually be collected from the fermentation liquid by a ligation of an ion-exchange resin method, precipitation and other known methods.

The present invention is illustrated more specifically by referring to the following Examples. However, nothing in these Examples shall be taken as a limitation upon the overall scope of the invention.

EXAMPLES

Example 1

Procurement of mutant AKIII gene (1).

(1) Cloning of wild-type AKIII gene.

The base sequence of *E. coli* AKIII gene (lysC) has been already reported [Cassan, M., Parsot, C., Cohen, G. N., and Patte, J. C., J. Biol. Chem. 261, 1052 (1986)]. It is known that an open reading frame (ORF) is composed of 1,347 base pairs, encoding a protein composed of 449 amino acid residues. This gene has an operator, and undergoes suppression with L-lysine. Therefore, in order to remove his operator region, the SD sequence and the region containing ORF alone were amplified through PCR, and cloned.

The overall genome DNA of E. coli K-12 MC1061 strain was produced by the method of Saito and Miura [Biochem. Biophys. Acta. 72, 619 (1963)], and two types of primers having sequences represented by SEQ ID NO:3 and SEQ ID NO:4 were formed. PCR was conducted by the method of H. A. Erlich et al. [PCR Technology, Stockton Press (1989)] using the same to amplify AKIII gene. The resulting DNA was digested with Bam HI and Ase I, then blunt-ended, and inserted into a Sma I site of a low copy vector pMW119 to construct pMLYSC2. This Sma I site is located downstream of a lacZ promoter present within the vector. When a recombinant DNA obtained by inserting a DNA fragment into the Sma I site of pMW119 is introduced into E. coli, the DNA fragment inserted is transcribed through transcription by controlling the lacZ promoter (FIG. 1).

(2). Cloning of mutant AKIII gene.

Plasmids having mutant AKIII gene, namely, pLYSC1*80, pLYSC1*117 and pLYSC1*126, as described in International Laid-Open Pamphlets WO94/11517 and WO95/16042 were digested with Eco RI and Hind III to cut out DNA fragments containing mutant AKIII gene. These fragments were inserted into an Eco RI-Hind III site of pMW119 to construct plasmids designated pMLYSC2*80, pMLYSC2*117 and pMLYSC2*126 respectively.

The plasmid pLYSC*80 can be produced from pLLC*8 according to the description in International Laid-Open Pamphlet WO4/11517. A strain obtained by introducing pLLC*80 into E. coli HB101 strain was designated AJ12750. It was deposited at the National Institute of Bioscience and Human Technology of the Agency of Industrial Science and Technology (No. 1-3, Higashi 1-chome, Tsukuba-shi, Ibaragiken, 305) under deposit No. FERM P-13136 on Sep. 1, 1992. This strain was transferred to international deposition under the Budapest Treaty on Nov. 4, 1993, and deposit No. FERM BP-4462 was newly allotted thereto. pLYSC2*117 and pLYSC2*126 are not yet deposited. However, since the mutation points thereof are disclosed in International Laid-Open Pamphlet WO94/11517, they can be easily prepared using PLYSC1*80 as a starting material.

(3). Study on conditions of selecting novel mutant AKIII gene.

A transformant obtained by introducing pMLYSC1 into a completely AK-deficient strain, E. coli GT3 (thrA1016b, metLM1005, lysC1004) was designated GT3/pMLYSC2. Likewise, GT3/pMLYSC2*80, GT3/pMLYSC2*117 and GT3/pMLYSC2*126 were obtained. GT3/pMLYSC2 strain has a plasmid containing wild-type lysC, and AKIII encoded in lysC of this plasmid is sole AK. Since wild-type AKIII which is sole AK in the presence of a considerable amount of L-lysine in the minimal medium is inhibited with L-lysine, L-threonine, L-isoleucine, L-methionine and diaminopimerinic acid (DAP) could not be synthesized, suppressing the growth thereof. With the expectation that a plasmid containing strain having mutant lysC in which inhibition with L-lysine is released can be grown on the minimal medium containing a considerable amount of L-lysine, a strain having an L-lysine resistance in the growth was selected, and a strain harboring a plasmid containing mutant lysC in which inhibition with L-lysine was released was thus selected. GT3/pMLYSC2 strain, GT3/pMLYSC2*80 strain, GT3/pMLYSC2*117 strain and GT3/pMLYSC2*126 strain were incubated on the minimal agar plate medium containing L-lysine at various concentrations to examine the growth inhibitory concentration and the conditions of selecting the plasmid-containing strains. The growth of the transformants on the minimal agar plate medium containing L-lysine at various concentrations is shown in Table 1. In Table 1, + indicates that a transform ant was grown, ± indicates that a transformant was slightly grown, and − indicates that no transformant was grown.

TABLE 1

| | Concentration of L-lysine and growth | | | | |
|---|---|---|---|---|---|
| | 0 | 0.2 | 0.4 | 0.6 | 0.8 (M) |
| GT3/pMLYSC2 | ± | − | − | − | − |
| GT3/pMLYSC2*80 | + | + | ± | − | − |
| GT3/pMLYSC2*117 | + | ± | − | − | − |
| GT3/pMLYSC2*126 | + | ± | − | − | − |

The growth of GT3/pMLYSC2 strain having wild-type lysC was completely suppressed in the addition area containing 0.2-M lysine. Further, the growth of GT3/pMLYSC2*80 strain, GT3/pMLYSC2*117 strain and GT3/pMLYSC2*126 strain having mutant lysC which are well known was also almost completely suppressed in the addition area containing 0.4-M L-lysine. Consequently, it was suggested that a mutant having a still higher degree of release of inhibition than mutant lysC known so far seemed likely to be obtained through the selection in the addition area containing 0.4-M L-lysine. It was identified that this growth inhibition was eliminated though the simultaneous addition of homoserine and diaminopimerinic acid.

In the test of introducing the mutation, a minimal agar medium M9 containing 0.4-M L-lysine was used in the selection of a plasmid-containing strain having mutant lysC. This medium is called selective medium in Example 1.

(4). Mutagenization of AKIII gene and procurement of mutant AKIII gene.

Two methods, namely, an in vitro mutagenization method in which a plasmid is directly treated with hydroxylamine and a PCR mutagenization method for providing various mutations in expectation of mutations other than mutation from cytosine to thymine with hydroxylamine were employed in the introduction of mutation into pMLYSC1 plasmid.

Two micrograms of pMLYSC2 were treated in 0.4-M hydroxylamine [a solution containing 100 $\mu$l of a mixture of 0.1-M $KH_2PO_4$ and 1-mM EDTA (pH 6.0) and a mixture of 1-M hydroxylamine and 1-mM EDTA (pH 6.0) and 2-$\mu$g DNA was adjusted to a total of 200 $\mu$l with the addition of water] at 75° C. for from 1 to 4 hours. The thus-treated DNA was purified with a glass powder, and then introduced into completely AK-deficient E. coli GT3 strain. The resulting transformant was spread on a complete medium (containing 1-% L-broth, 0.5-% yeast extract, 0.5-% NaCl, 50 mg/liter of ampicillin and 1.5-% agar) to form colonies. The colonies were replicated on the selective medium, and strains capable of being grown on the selective medium were selected as candidate strains.

The random mutagenization through PCR was conducted by the method of C. Cadwell et al. (Cadwell, C. and G. F. Joyce, PCR methods Applic. 2, 28, (1982)]. That is, a lysC fragment was amplified by the above-mentioned method using pMLYSC2 and M13 universal primer. This fragment was digested with Eco RI and Hind III, and then inserted into an Eco RI-Hind III site of pMW119 to introduce the same into completely AK-deficient E. coli GT3. The transformant was spread on a complete medium (containing 1-% L-broth, 0.5-% bacto tryptone, 0.5-% yeast extract, 0.5-% NaCl, 50 mg/liter of ampicillin and 1.5-% agar) to form colonies. The colonies were replicated on the selective medium, and strains capable of being grown on the selective medium were selected as candidate strains.

The plasmids were recovered from a total of 47 candidate strains obtained above, namely, 44 strains resulting from the mutagenization with hydroxylamine, 3 strains resulting from the random mutagenization through PCR. The mutant lysC base sequences were determined, and the mutation points were identified. The determination of the base sequences was conducted by a usual method using a DNA sequencer ABI Model 373A (supplied by ABI). As a result, mutant AKIII strains having 4 types (Nos. 1, 6, 14 and 21) of mutation points could be obtained from strains resulting from the mutagenization with hydroxylamine, and mutant AKIII strains having 3 types (Nos. 28, 29 and 30) of mutation points from strains resulting from the random mutagenization though PCR could be obtained (Table 2).

TABLE 2

| mutant lysC | mutagenization method | mutation point (amino acid) |
| --- | --- | --- |
| No. 1 | HYDROXYLAMINE | ACG → ATG(344Thr → Met) |
| No. 6 | HYDROXYLAMINE | GAG → AAG(250Glu → Lys) |
| No. 14 | HYDROXYLAMINE | GAA → AAA(346Glu → Lys) |
|  |  | CTT → TTT(374Leu → Phe) |
| No. 21 | HYDROXYLAMINE | GAG → AAG(250Glu → Lys) |
|  |  | ACG → ATG(364Thr → Met) |
| No. 28 | P C R | GAT → GGT(202Asp → Gly) |
|  |  | TCT → CCT(321Ser → Pro) |
| No. 29 | P C R | CGC → AGC(283Arg → Ser) |
|  |  | GCG → ACG(333Ala → Thr) |
|  |  | TCG → ACG(338Ser → Thr) |
|  |  | GAA → GAT(346Glu → Asp) |
|  |  | AAC → AGC(414Asn → Ser) |
| No. 30 | P C R | ATG → AAG(318Met → Lys) |
|  |  | TCT → CCT(321Ser → Pro) |
|  |  | GTT → TTT(328Val → Phe) |
|  |  | GTG → GGG(349Val → Gly) |
|  |  | GAG → GTG(405Glu → Val) |

These seven plasmids (pMLYSC2*Y1, pMLYSC2*Y6, pMLYSC2*Y14, pMLYSC2*Y21, pMLYSC2*Y28, pMLYSC2*Y29 and pMLYSC2*Y30) were introduced into completely AK-deficient GT3 strain, and cell-free extracts were prepared from the transformants. The enzymatic activity of AKIII was measured using the same. The production of the cell-free extracts and the measurement of the enzymatic activity of AKIII were conducted by the method of E. R. Stadtman et al. (Stadtman, E. R., Cohen, G. N., LeBras, G., and Robichon-Szulmajster, H., J. Biol. Chem. 236, 2033 (1961)]. Further, in the measurement of the AKIII enzymatic activity, L-lysine at various concentrations was added to the enzyme reaction solution to examine the degree of release of inhibition with L-lysine.

The results are shown in Table 3. The degree of release of inhibition refers to a ratio of an AK residual activity in the presence of 0.4-M L-lysine to an AK activity in the absence of L-lysine.

TABLE 3

| Strain | Degree of release of feedback inhibition |
| --- | --- |
| GT3/pMLYSC2*80 | 75 (%) |
| GT3/pMLYSC2*117 | 76 |
| GT3/pMLYSC2*Y1 | 56 |
| GT3/pMLYSC2*Y6 | 127 |
| GT3/pMLYSC2*Y14 | 87 |
| GT3/pMLYSC2*Y21 | 117 |
| GT3/pMLYSC2*Y28 | 114 |
| GT3/pMLYSC2*Y29 | 99 |
| GT3/pMLYSC2*Y30 | 116 |

As is clear from the above-mentioned results, mutant AKIII which had the higher degree of release of inhibition than the conventional typical mutant AKIII (mutant AKIII encoded in pMLYSC2*80 and pMLYSC2*117) could be obtained by the selection method used this time. A specific activity based on the total protein is usually influenced by the growth condition of cells or the preparation of samples. The specific activity thereof was equal to those of wild-type and the conventional mutants, and almost no decrease in the activity by introducing the mutation was observed. Accordingly, it was expected that the activity center of AKIII and the control site with L-lysine thereof were independent from each other.

Example 2

Procurement of mutant AKIII gene (2).

A lysC gene in which the 358th Ser was substituted with Leu was prepared by introducing the site specific mutation using an LA PCR in vitro Mutagenesis Kit (supplied by Takara Shuzo Co., Ltd.). At this time, pLYSC1 described in International Laid-Open Pamphlet WO94/11517 and WO95/16042 was used as a template, and the primer described in SEQ ID NO:5 as a primer for introduction of mutation respectively. Both terminals of a PCR amplification fragment was cleaved with Eco RI and Hind III, and the fragment cleaved was ligated with a fragment obtained by cleaving pUC19 with Eco RI and Hind III of pUC19 to form pLYSC358L. Mutant AKIII gene in which the 354th Ser was mutagenized into Ile or Val was prepared in the above-mentioned manner except that the primer described in SEQ ID NO:6 or SEQ ID NO:7 was used as a primer. This gene was ligated with a fragment obtained by cleaving pUC19 with Eco RI and Hind III. Thus, pLYSC345I and pLYSC354V were formed.

Fragments containing lysC which were obtained by cleaving pLYSC1*48, pLYSC1*117, PLYSC*126, pLYSC1*150 and pLYSC1*158 with Eco RI and Hind III were inserted into an Eco RI-Hind III cleavage site of pUC19, and the resulting fragments were designated pLYSC2*48, pLYSC2*117, pLYSC2*126, pLYSC2*150, and pLYSC2*158 respectively. International Laid-Open Pamphlets WO94/11517 and WO95/16042 disclose the structure of pLYSC1 and the sites of mutation points of pLYSC1*48, pLYSC2*117, pLYSC1*126, pLYSC2*150 and pLYSC2*158. Therefore, these plasmids can be prepared from the above-mentioned pLYSC1*80.

Subsequently, mutant lysC gene having two types of mutations was prepared using an Ssp I cleavage site present in the vicinity of the center of mutation points of the thus-obtained monobasic mutant lysC and an Ssp I cleavage site located downstream of lysC in pUC19. That is, pU2547M was prepared by ligating an Ssp I fragment containing a lysC gene upstream region of pLYSC2*48 with an Ssp I fragment containing a lysC gene downstream region of pLYSC2*158; pU2347M was prepared by ligating an Ssp I fragment containing a lysC gene upstream region of pLYSC2*126 with an Ssp I fragment containing a lysC gene downstream region of pLYSC2*158; pU2545L was prepared by ligating an Ssp I fragment containing a lysC gene upstream region of pLYSC2*48 with an Ssp I fragment containing a lysC gene downstream region of pLYSC2*117; pU2358L was prepared by ligating an Ssp I fragment containing a lysC gene upstream region of pLYSC2*126 with an Ssp I fragment containing a lysC gene downstream region of pLYSC358L; pU2345V was prepared by ligating an Ssp I fragment containing a lysC gene upstream region of pLYSC2*126 with an Ssp I fragment containing a lysC gene downstream region of pLYSC345V; and pU2345I was prepared by ligating an Ssp I fragment containing a lysC gene upstream region of pLYSC2*126 with an Ssp I fragment containing a lysC gene downstream region of pLYSC345I. Since mutation points of pLYSC2*150 and pLYSC2*126 are located more upstream than Ssp I cleavage sites, dibasic mutant lysC having these two mutation points was prepared as follows. First, a DNA fragment having two mutation points was amplified using pLYSC26*126 as a template, an oligonucleotide described in SEQ ID NO:8 as a primer and the above-mentioned kit. Subsequently, both terminals of the resulting DNA fragment were cleaved with Eco RI and Hind III, and ligated with a fragment obtained by cleaving pUC19 with Eco RI and Hind III. The thus-obtained product was designated pU1823D.

The degree of release of inhibition of the thus-obtained dibasic mutant lysC gene product (AKIII) relative to Lys was measured as described in Example 1. Consequently, the degree of release of inhibition of any dibasic mutant AKIII was higher than that of monobasic mutant AKIII (Table 4). Incidentally, mutant lysC in pLYSC582L, pLYSC345I and pLYSC345V is a novel mutant gene. In each of the gene products, the feedback inhibition with lysine is released, and the ligation with the other mutation improves more the degree of release of inhibition. The product is also useful as an intermediate for construction of the dibasic mutant AKIII.

TABLE 4

| Strain | Mutation point (amino acid) | Degree of release of feedback inhibition (%) |
|---|---|---|
| GT3/pLYSC2*48 | 325Leu → Phe | 12 |
| GT3/pLYSC2*117 | 345Ser → Leu | 75 |
| GT3/pLYSC2*126 | 323Gly → Asp | 5 |
| GT3/pLYSC2*150 | 318Met → Ile | 8 |
| GT3/pLYSC2*158 | 347Val → Met | 3 |
| GT3/pU345I | 345Ser → Ile | 108 |
| GT3/pU345V | 345Ser → Val | 98 |
| GT3/pU358L | 358Ser → Leu | 3 |
| GT3/pU2547M | 325Leu → Phe, 347Val → Met | 90 |
| GT3/pU2347M | 323Gly → Asp, 347Val → Met | 94 |
| GT3/pU2545L | 325Leu → Phe, 345Ser → Leu | 172 |
| GT3/pU2358L | 323Gly → Asp, 358Ser → Leu | 18 |
| GT3/pU2345V | 323Gly → Asp, 345Ser → Val | 109 |
| GT3/pU2345I | 323Gly → Asp, 345Ser → Ile | 152 |
| GT3/pU1823D | 318Met → Ile, 323Gly → Asp | 91 |

Example 3

Production of L-lysine through fermentation using a strain having introduced therein mutant DDPS gene and mutant AKIII gene.

The effect for production of L-lysine with respect to mutant DDPS gene and mutant AKIII gene is described in International Laid-Open Pamphlet WO95/16042. In order to improve this effect, mutant AKIII gene obtained in Example 1 was caused to co-exist with mutant DDPS gene.

A strain obtained by introducing plasmid RSF24P having mutant DDPS gene described in International Laid-Open Pamphlet WO95/16042 into *E. coli* JM109 strain was designated AJ12395. It was deposited at the National Institute of Bioscience and Human Technology of the Agency of Industrial Science and Technology (No. 1-3, Higashi 1-chome, Tsukubashi, Ibaragi-ken, 305) under deposit No. FERM P-13935 on Oct. 28, 1993. This strain was transferred to international deposition under the Budapest Treaty on Nov. 1, 1994, and deposit No. FERM BP-4858 was newly allotted thereto.

Figure 2:
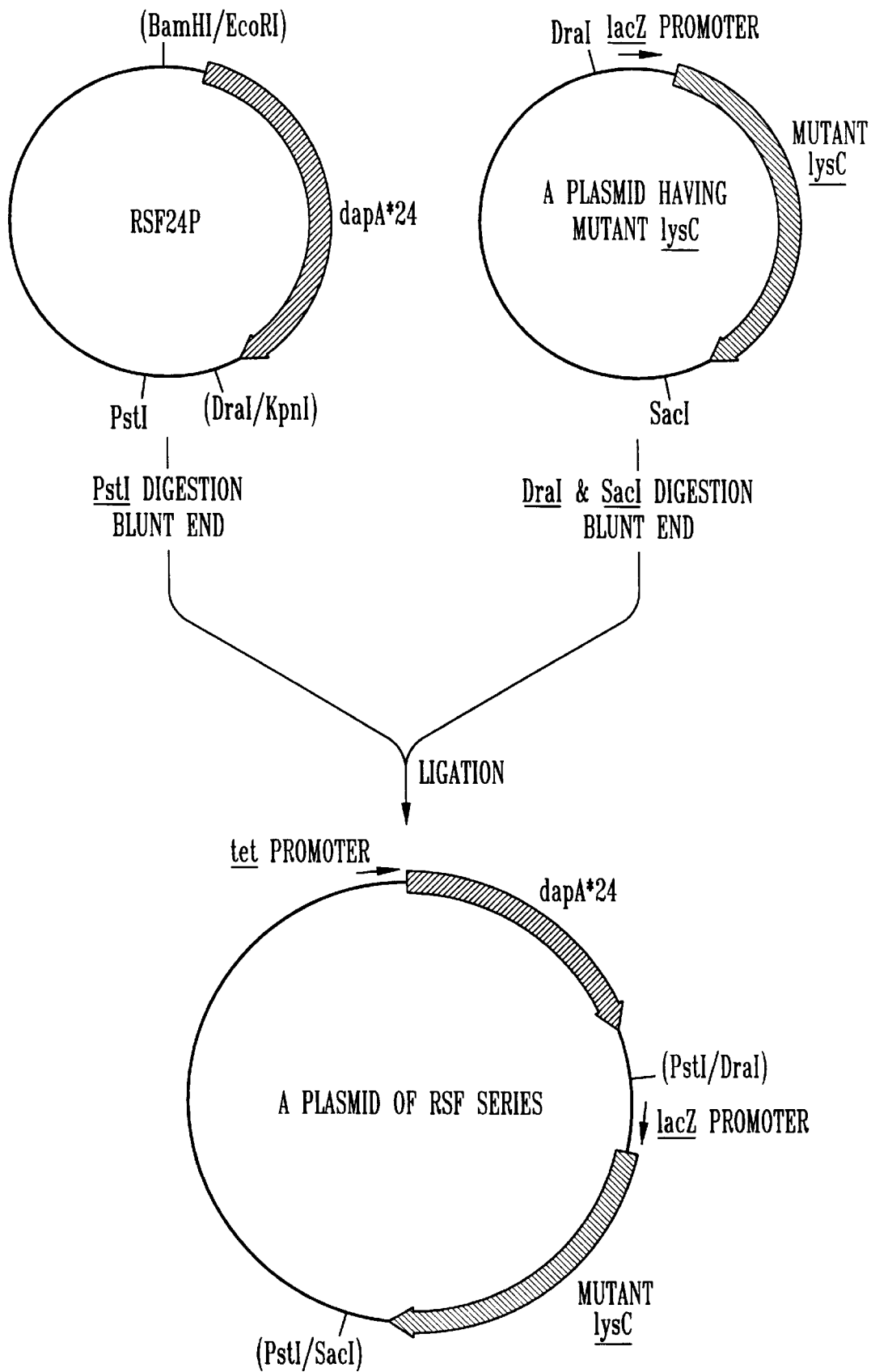
FIG. 2 illustrates the preparation process for plasmids of RSFD series.

Plasmids RSFDY1, RSFDY6, RSFDY14, RSFDY21, RSFDY28, RSFDY29, RSFDY30, RSFD2547M, RSFD2347M, RSFD2545L, RSFD2358L, RSFD2345V, RSFD23451 and RSFD1823D were prepared as shown in FIG. 2 from one type selected from plasmids containing mutant AKIII gene, pMLYSC2*Y1, pMLYSC2*Y6, pMLYSC2*Y14, pMLYSC2*Y21, pMLYSC2*Y28, pMLYSC2*Y29, pMLYSC2*Y30, pU2547M, pU2347M, pU2545L, pU2358L, pU2545V, pU2345I and pU1823D.

Plasmid RSFD80 described in International Laid-Open Pamphlet WO95/16042 was used as a control. A strain obtained by introducing plasmid RSFD80 into *E. coli* JM109 strain was designated AJ12396. It was deposited at the National Institute of Bioscience and Human Technology of the Agency of Industrial Science and Technology (No. 1-3, Higashi 1-chome, Tsukuba-shi, Ibaragi-ken, 305) under deposit No. FERM P-13936 on Oct. 28, 1993. This strain was transferred to international deposition under Budapest Treaty on Nov. 1, 1994, and deposit No. FERM BP-4859 was newly allotted thereto.

The above-obtained plasmids RSFDY1, RSFDY6, RSFDY14, RSFDY21, RSFDY28, RSFDY29, RSFDY30, RSFD2547M, RSFD2347M, RSFD2545L, RSFD2358L, RSFD2345V, RSFD23451 and RSFD1823D were introduced into B-399 strain in a usual manner to form L-lysine-productive strains. The lysine productivity of the above-mentioned strains was evaluated. The evaluation of the lysine productivity was also conducted with respect to B-399/RSFD80 as a control. A method of obtaining B-399 strain is described in International Open Pamphlet WO95/16042.

The incubation was conducted in the L-lysine-productive culture medium at 37° C. for an incubation time of 48 hours through stirring at from 114 to 116 rpm according to the method described in International Laid-Open Pamphlet WO95/16042. The results are shown in Table 5.

TABLE 5

| Strain | Amount of L-lysine hydrochloride formed |
|---|---|
| B-399/RSFD80 | 9.2 g/L |
| B-399/RSFDY1 | 9.4 g/L |
| B-399/RSFDY6 | 9.6 g/L |
| B-399/RSFDY14 | 9.6 g/L |
| B-399/RSFDY21 | 9.5 g/L |
| B-399/RSFDY28 | 9.6 g/L |
| B-399/RSFDY29 | 9.5 g/L |
| B-399/RSFDY30 | 9.3 g/L |
| B-399/RSFD2547M | 9.6 g/L |
| B-399/RSFD2347M | 9.5 g/L |
| B-399/RSFD2545L | 9.6 g/L |
| B-399/RSFD2358L | 9.3 g/L |
| B-399/RSFD2345V | 9.4 g/L |

TABLE 5-continued

| Strain | Amount of L-lysine hydrochloride formed |
| --- | --- |
| B-399/RSFD23451 | 9.3 g/L |
| B-399/RSFD1823D | 9.6 g/L |

Example 4

Production of L-lysine through fermentation using a strain having introduced therein mutant DDPS gene and mutant AKIII gene (2).

It was identified in Example 3 that the productivity of L-lysine could be improved by making bacteria of the genus Escherichia to have mutant DDPS gene and mutant AKIII gene. The test was conducted as to whether this effect can be maintained even when a host is changed.

*E. coli* W3110 (tyrA) strain was used as a host. W3110 (tyrA) strain is described in detail in European Patent Laid-Open No. 488,424/1992. European Patent Laid-Open No 488,424/1992 describes a large number of strains obtained by introducing a plasmid into W3110 (tyrA) strain. For example, a strain obtained by introducing plasmid pHATerm was designated *E. coli* W3110 (tyrA)/pHATerm strain. It was internationally deposited at the National Institute of Bioscience and Human Technology of the Agency of Industrial Science and Technology (No. 1-3, Higashi 1-chome, Tsukubashi, Ibaragi-ken, 305) on Nov. 18, 1991 under the Budapest Treaty, and deposit No. FERM BP-3653 was allotted thereto. W3110 (tyrA) strain can also be obtained by removing plasmid pHATerm from this *E. coli* W3110 (tyrA)/pHATerm strain. The removal of the plasmid can be conducted in a usual manner.

The plasmids containing mutant DDPS gene and mutant AKIII gene obtained in Example 3, namely, RSFDY1, RSFDY6, RSFDY14, RSFDY21, RSFDY28, RSFDY29, RSFDY30, RSFD2547M, RSFD2347M, RSFD2545L, RSFD2358L, RSFD2345V RSFD23451 and RSFD1823D were introduced into the above-obtained W3110 (tyrA) strain, and the L-lysine productivity was evaluated as in Example 3. As a control, W3110 (tyrA)/RSFD80 was produced by introducing RSFD80 into W3110 (tyrA) strain, and the L-lysine productivity of this strain was also evaluated. The results are shown in Table 6.

TABLE 6

| Strain | Amount of L-lysine hydrochloride formed |
| --- | --- |
| W3110(tyrA)/RSFD80 | 8.9 g/L |
| W3110(tyrA)/RSFDY1 | 9.1 g/L |
| W3110(tyrA)/RSFDY6 | 9.3 g/L |
| W3110(tyrA)/RSFDY14 | 9.3 g/L |
| W3110(tyrA)/RSFDY21 | 9.2 g/L |
| W3110(tyrA)/RSFDY28 | 9.3 g/L |
| W3110(tyrA)/RSFDY29 | 9.2 g/L |
| W3110(tyrA)/RSFDY30 | 9.0 g/L |
| W3110(tyrA)/RSFD2547M | 9.3 g/L |
| W3110(tyrA)/RSFD2347M | 9.2 g/L |
| W3110(tyrA)/RSFD2545L | 9.3 g/L |
| W3110(tyrA)/RSFD2358L | 9.0 g/L |
| W3110(tyrA)/RSFD2345V | 9.1 g/L |
| W3110(tyrA)/RSFD2345I | 9.0 g/L |
| W3110(tyrA)/RSFD1823D | 9.3 g/L |

Example 5

Production of L-threonine through fermentation using a strain having introduced therein mutant AKIII gene.

Figure 3:
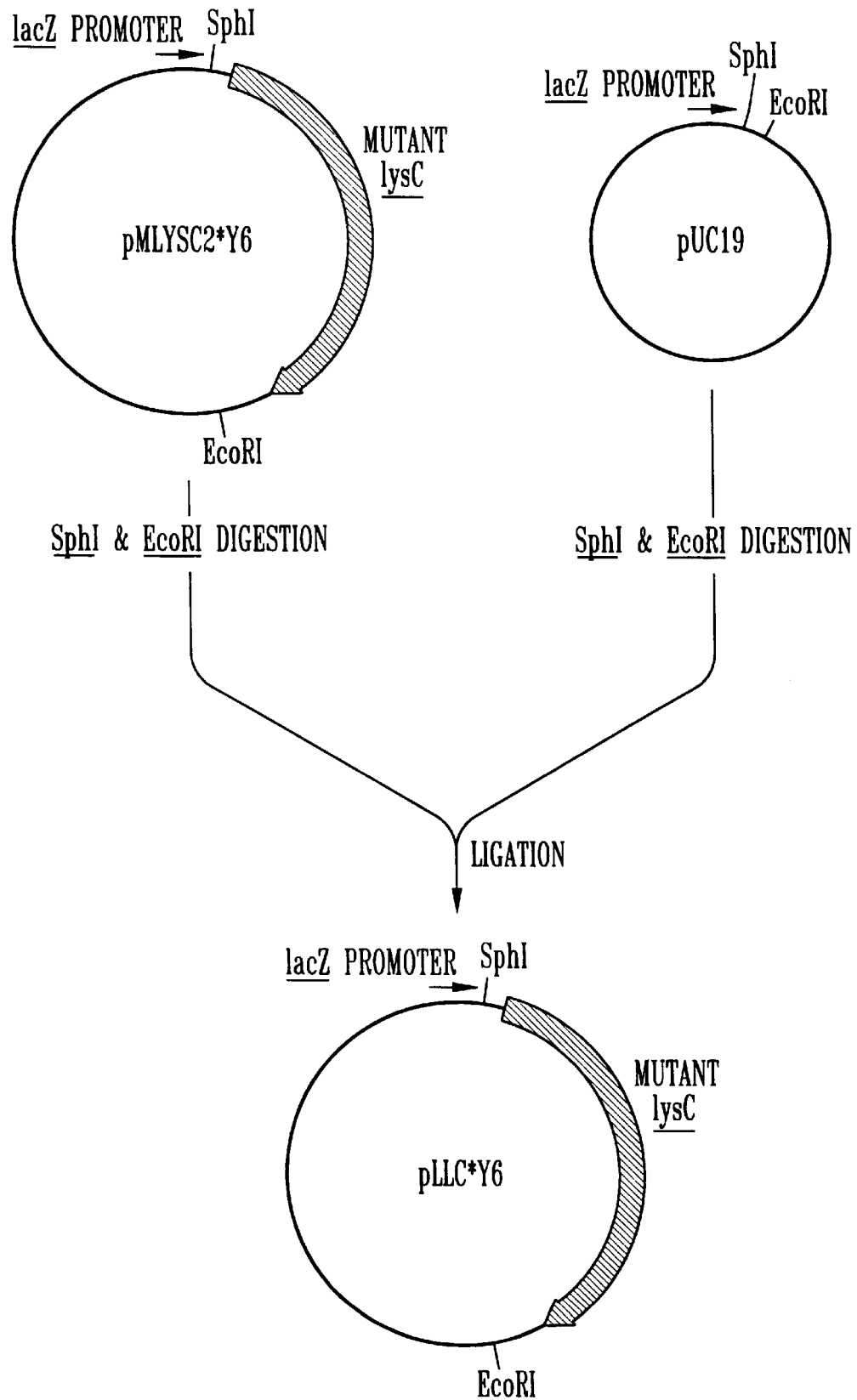
FIG. 3 illustrates the preparation process for pLLC*Y6.

As *E. coli* threonine-productive strain, B-3996 strain has the highest productivity among those which are known at present. Therefore, in evaluating mutant AKIII, B-3996 strain was used as a host. This B-3996 strain is described in U.S. Pat. No. 5,175,107, and listed as deposited in Research Institute for Genetics and Industrial Microorganism Breeding under deposit No. BKIIM B-3996. Further, as mutant AKIII gene for evaluation, three types of mutant genes (mutant AKIII genes of RSFDY6, RSFE254M and RSFD1823D) among mutant genes having the high L-lysine productivity in Example 4 were selected, and subjected to the test. First, in order to increase the amount of expression of mutant AKIII gene, mutant AKIII gene present in pMLYSC2*Y6 was ligated with the downstream region of lacZ promoter of pUC19 (supplied by Takara Shuzo Co., Ltd.). The thus-formed novel plasmid was designated pLLC*Y6 (FIG. 3). Since in pU2547M and pU1823D, mutant AKIII gene is downstream of lacZ promoter of pUC19 (supplied by Takara Shuzo Co., Ltd.), it was used as such.

These plasmids were introduced into B-3996 strain usual manner, and the evaluation was conducted. The incubation was conducted by the method described in International Laid-Open Pamphlet WO94/11517.

pLLC*Y6, pU2547M and pU1823D were transformed into B3996 strain, and the transformants were incubated in the presence or absence of 1 g/liter of lysine. The host B-3996 strain alone and B-3996/pLLC*80 described in International Laid-Open Pamphlet WO94/11517 were used as controls.

The results are shown in Table 7. The lysine sensitivity in Table 7 refers to a ratio of (yield of sugar consumed in the presence of lysine) to (yield of sugar consumed in the absence of lysine). In B-3996 strain, the decrease in the yield of sugar consumed in the incubation in the presence of lysine is approximately 0.74 relative to that in the area of incubation in the absence of lysine; and in B-3996/pLLC*80, the decrease in the yield of sugar consumed in the incubation in the presence of lysine is approximately 0.90 relative to that in the area of incubation in the absence of lysine. Mutant AKIII genes newly obtained this time are slightly superior in the threonine productivity and the lysine sensitivity.

TABLE 7

| Strain | Amount of L-lysine added (g/L) | Yield of sugar consumed (%) | Lysine sensitivity |
| --- | --- | --- | --- |
| B-3996 | 0 | 30.7 | |
| | 1 | 22.6 | 0.74 |
| B-3996/pLLC*80 | 0 | 39.7 | |
| | 1 | 35.6 | 0.90 |
| B-3996/pLLC*Y6 | 0 | 40.5 | |
| | 1 | 39.2 | 0.97 |
| B-3996/pU2547M | 0 | 40.7 | |
| | 1 | 39.5 | 0.97 |
| B-3996/pU1823D | 0 | 41.4 | |
| | 1 | 40.5 | 0.98 |

The present invention has enabled production of mutant AKIII gene derived from bacteria of the genus Escherichia in which feedback inhibition with L-lysine is released well. An L-amino-acid-productive strain which is more improved than before can be formed by introducing the above-mentioned gene into bacteria of the genus Escherichia. It is possible to provide a process for producing an L-amino acid through fermentation which is superior to the conventional process by using this L-amino acid-productive strain.

This application is based upon Japanese patent Application No. 272114/1996 filed with the Japanese Patent Office on Oct. 15, 1996, the entire contents of which are herein incorporated by reference.

Having now fully described the invention, it will be apparent to one of ordinary skill in the art that many changes and modifications can be made thereto without departing from the spirit or scope of the invention as set forth herein.

---

---

What is claimed as new and desired to be secured by Letters Patent of the United States:

1. An isolated nucleic acid molecule encoding a mutant of the aspartokinase set forth in SEQ ID NO:2, wherein the mutations are selected from the group consisting of:
   the aspartic acid at position 202 is substituted with another amino acid,
   the glutamic acid at position 250 is substituted with another amino acid,
   the arginine at position 283 of the mutant is substituted with another amino acid,
   the serine at position 321 is substituted with another amino acid,
   the valine at position 328 is substituted with another amino acid,
   the alanine at position 333 is substituted with another amino acid,
   the serine at position 338 is substituted with another amino acid,
   the threonine at position 344 is substituted with another amino acid,
   the glutamic acid at position 346 is substituted with another amino acid,
   the serine at position 358 is substituted with another amino acid,
   the threonine at position 364 is substituted with another amino acid,
   the leucine at position 374 is substituted with another amino acid,
   the glutamic acid at position 405 is substituted with another amino acid, and
   the asparagine at position 414 is substituted with another amino acid.

2. An isolated nucleic acid molecule encoding a mutant of the aspartokinase set forth in SEQ ID NO:2, wherein:
   the methionine at position 318 of the mutant is substituted with another amino acid, and
   the glycine at position 323 of the mutant is substituted with another amino acid.

3. An isolated nucleic acid molecule encoding a mutant of the aspartokinase set forth in SEQ ID NO:2, wherein:
   the leucine at position 325 of the mutant is substituted with another amino acid, and
   the valine at position 347 of the mutant is substituted with another amino acid.

4. An isolated nucleic acid molecule encoding a mutant of the aspartokinase set forth in SEQ ID NO:2, wherein:
   the glycine at position 323 of the mutant is substituted with another amino acid, and
   the valine at position 347 of the mutant is substituted with another amino acid.

5. An isolated nucleic acid molecule encoding a mutant of the aspartokinase set forth in SEQ ID NO:2, wherein:
the leucine at position 325 of the mutant is substituted with another amino acid, and
the serine at position 345 of the mutant is substituted with another amino acid.

6. An isolated nucleic acid encoding a mutant of the aspartokinase set forth in SEQ ID NO:2, wherein:
the glycine at position 323 of the mutant is substituted with another amino acid, and
the serine at position 358 of the mutant is substituted with another amino acid.

7. The isolated nucleic acid molecule of claim 1, wherein:
the threonine at position 344 of the mutant is substituted with another amino acid.

8. The isolated nucleic acid molecule of claim 1, wherein:
the glutamic acid at position 250 of the mutant is substituted with another amino acid.

9. The isolated nucleic acid molecule of claim 1, wherein:
the glutamic acid at position 346 of the mutant is substituted with another amino acid, and
the at position 374 of the mutant is substituted with another amino acid.

10. The isolated nucleic acid molecule of claim 1, wherein:
the glutamic acid at position 250 of the mutant is, and
the threonine at position 364 of the mutant is substituted with another amino acid.

11. The isolated nucleic acid molecule of claim 1, wherein:
the aspartic acid at position 202 of the mutant is substituted with another amino acid, and
the serine at position 321 of the mutant is substituted with another amino acid.

12. The isolated nucleic acid molecule of claim 1, wherein:
the amino acid at position 283 of the mutant is not arginine,
the amino acid at position 333 of the mutant is not alanine,
the amino acid at position 338 of the mutant is not serine,
the amino acid at position 346 of the mutant is not glutamic acid, and
the amino acid at position 414 of the mutant is not asparagine.

13. An isolated nucleic acid molecule encoding a mutant of the aspartokinase set forth in SEQ ID NO:2, wherein:
the methionine at position 318 of the mutant is substituted with another amino acid,
the serine at position 321 of the mutant is substituted with another amino acid,
the valine at position 328 of the mutant is substituted with another amino acid,
the valine at position 349 of the mutant is substituted with another amino acid, and
the glutamic acid at position 405 of the mutant is substituted with another amino acid.

14. The isolated nucleic acid molecule of claim 2, wherein:
the amino acid at position 318 of the mutant is isoleucine, and
the amino acid at position 323 of the mutant is aspartic acid.

15. The isolated nucleic acid molecule of claim 3, wherein:

the amino acid at position 325 of the mutant is phenylalanine, and
the amino acid at position 347 of the mutant is methionine.

16. The isolated nucleic acid molecule of claim 4, wherein:
the amino acid at position 323 of the mutant is aspartic acid, and
the amino acid at position 347 of the mutant is methionine.

17. The isolated nucleic acid molecule of claim 5, wherein:
the amino acid at position 325 of the mutant is phenylalanine, and
the amino acid at position 345 of the mutant is leucine.

18. An isolated nucleic acid molecule encoding a mutant of the aspartokinase set forth in SEQ ID NO:2, wherein:
the amino acid at position 323 of the mutant is aspartic acid, and
the amino acid at position 358 of the mutant is leucine.

19. The isolated nucleic acid molecule of claim 1, wherein:
the amino acid at position 344 of the mutant is methionine.

20. The isolated nucleic acid molecule of claim 1, wherein:
the amino acid at position 250 of the mutant is lysine.

21. The isolated nucleic acid molecule of claim 1, wherein:
the amino acid at position 346 of the mutant is lysine, and
the amino acid at position 374 of the mutant is phenylalanine.

22. The isolated nucleic acid molecule of claim 1, wherein:
the amino acid at position 250 of the mutant is lysine, and
the amino acid at position 364 of the mutant is methionine.

23. The isolated nucleic acid molecule of claim 1, wherein:
the amino acid at position 202 of the mutant is glycine, and
the amino acid at position 321 of the mutant is proline.

24. The isolated nucleic acid molecule of claim 1, wherein:
the amino acid at position 283 of the mutant is serine,
the amino acid at position 333 of the mutant is threonine,
the amino acid at position 338 of the mutant is threonine,
the amino acid at position 346 of the mutant is aspartic acid, and
the amino acid at position 414 of the mutant is serine.

25. An isolated nucleic acid molecule encoding a mutant of the aspartokinase set forth in SEQ ID NO:2, wherein:
the amino acid at position 318 of the mutant is lysine,
the amino acid at position 321 of the mutant is proline,
the amino acid at position 328 of the mutant is phenylalanine,
the amino acid at position 349 of the mutant is glycine, and
the amino acid at position 405 of the mutant is valine.

26. The isolated nucleic acid molecule of claim 1, wherein the molecule is DNA.

27. A recombinant DNA molecule comprising the isolated nucleic molecule of claim 26.

28. The recombinant DNA molecule of claim 27, wherein the molecule is capable of autonomous replication in a strain of *Escherichia coli*.

29. An *Escherichia coli* host cell transformed with a recombinant DNA molecule comprising the isolated nucleic acid molecule of claim 1.

30. A process for producing an L-amino acid comprising the steps of:
   (a) incubating the strain of claim 29 in a fermentation medium, thereby causing the L-amino acid to be produced and accumulated in the fermentation medium; and
   (b) collecting the L-amino acid from the fermentation medium.

31. The process of claim 30, wherein the L-amino acid is L-lysine or L-threonine.

32. The isolated nucleic acid molecule of claim 2, wherein the molecule is DNA.

33. A recombinant DNA molecule comprising the isolated nucleic molecule of claim 32.

34. The recombinant DNA molecule of claim 33, wherein the molecule is capable of autonomous replication in a strain of *Escherichia coli*.

35. An *Escherichia coli* host cell transformed with a recombinant DNA molecule comprising the isolated nucleic acid molecule of claim 2.

36. A process for producing an L-amino acid comprising the steps of:
   (a) incubating the transformed host cell of claim 35 in a fermentation medium, thereby causing the L-amino acid to be produced and accumulated in the fermentation medium; and
   (b) collecting the L-amino acid from the fermentation medium.

37. The process of claim 36, wherein the L-amino acid is L-lysine or L-threonine.

38. The isolated nucleic acid molecule of claim 3, wherein the molecule is DNA.

39. A recombinant DNA molecule comprising the isolated nucleic molecule of claim 38.

40. The recombinant DNA molecule of claim 39, wherein the molecule is capable of autonomous replication in a strain of *Escherichia coli*.

41. An *Escherichia coli* host cell transformed with a recombinant DNA molecule comprising the isolated nucleic acid molecule of claim 3.

42. A process for producing an L-amino acid comprising the steps of:
   (a) incubating the transformed host cell of claim 41 in a fermentation medium, thereby causing the L-amino acid to be produced and accumulated in the fermentation medium; and
   (b) collecting the L-amino acid from the fermentation medium.

43. The process of claim 42, wherein the L-amino acid is L-lysine or L-threonine.

44. The isolated nucleic acid molecule of claim 4, wherein the molecule is DNA.

45. A recombinant DNA molecule comprising the isolated nucleic molecule of claim 44.

46. The recombinant DNA molecule of claim 45, wherein the molecule is capable of autonomous replication in a strain of *Escherichia coli*.

47. An *Escherichia coil* host cell transformed with a recombinant DNA molecule comprising the isolated nucleic acid molecule of claim 4.

48. A process for producing an L-amino acid comprising the steps of:
   (a) incubating the transformed host cell of claim 47 in a fermentation medium, thereby causing the L-amino acid to be produced and accumulated in the fermentation medium; and
   (b) collecting the L-amino acid from the fermentation medium.

49. The process of claim 48, wherein the L-amino acid is L-lysine or L-threonine.

50. The isolated nucleic acid molecule of claim 5, wherein the molecule is DNA.

51. A recombinant DNA molecule comprising the isolated nucleic molecule of claim 50.

52. The recombinant DNA molecule of claim 51, wherein the molecule is capable of autonomous replication in a strain of *Escherichia coli*.

53. An *Escherichia coli* host cell transformed with a recombinant DNA molecule comprising the isolated nucleic acid molecule of claim 5.

54. A process for producing an L-amino acid comprising the steps of:
   (a) incubating the transformed host cell of claim 53 in a fermentation medium, thereby causing the L-amino acid to be produced and accumulated in the fermentation medium; and
   (b) collecting the L-amino acid from the fermentation medium.

55. The process of claim 54, wherein the L-amino acid is L-lysine or L-threonine.

56. The isolated nucleic acid molecule of claim 6, wherein the molecule is DNA.

57. A recombinant DNA molecule comprising the isolated nucleic molecule of claim 56.

58. The recombinant DNA molecule of claim 57, wherein the molecule is capable of autonomous replication in a strain of *Escherichia coli*.

59. An *Escherichia coli* host cell transformed with a recombinant DNA molecule comprising the isolated nucleic acid molecule of claim 6.

60. A process for producing an L-amino acid comprising the steps of:
   (a) incubating the transformed host cell of claim 59 in a fermentation medium, thereby causing the L-amino acid to be produced and accumulated in the fermentation medium; and
   (b) collecting the L-amino acid from the fermentation medium.

61. The process of claim 60, wherein the L-amino acid is L-lysine or L-threonine.

62. The isolated nucleic acid molecule of claim 13, wherein the molecule is DNA.

63. A recombinant DNA molecule comprising the isolated nucleic molecule of claim 62.

64. The recombinant DNA molecule of claim 63, wherein the molecule is capable of autonomous replication in a strain of *Escherichia coli*.

65. An *Escherichia* coli host cell transformed with a recombinant DNA molecule comprising the isolated nucleic acid molecule of claim 13.

66. A process for producing an L-amino acid comprising the steps of:
   (a) incubating the transformed host cell of claim 65 in a fermentation medium, thereby causing the L-amino acid to be produced and accumulated in the fermentation medium; and (b) collecting the L-amino acid from the fermentation medium.

67. The process of claim 66, wherein the L-amino acid is L-lysine or L-threonine.

68. The isolated nucleic acid molecule of claim 18, wherein the molecule is DNA.

69. A recombinant DNA molecule comprising the isolated nucleic molecule of claim 68.

70. The recombinant DNA molecule of claim 69, wherein the molecule is capable of autonomous replication in a strain of *Escherichia coli*.

71. An *Escherichia coli* host cell transformed with a recombinant DNA molecule comprising the isolated nucleic acid molecule of claim 18.

72. A process for producing an L-amino acid comprising the steps of:
  (a) incubating the transformed host cell of claim 71 in a fermentation medium, thereby causing the L-amino acid to be produced and accumulated in the fermentation medium; and
  (b) collecting the L-amino acid from the fermentation medium.

73. The process of claim 72, wherein the L-amino acid is L-lysine or L-threonine.

74. The isolated nucleic acid molecule of claim 25, wherein the molecule is DNA.

75. A recombinant DNA molecule comprising the isolated nucleic molecule of claim 74.

76. The recombinant DNA molecule of claim 75, wherein the molecule is capable of autonomous replication in a strain of *Escherichia coli*.

77. An *Escherichia coli* host cell transformed with a recombinant DNA molecule comprising the isolated nucleic acid molecule of claim 25.

78. A process for producing an L-amino acid comprising the steps of:
  (a) incubating the transformed host cell of claim 77 in a fermentation medium, thereby causing the L-amino acid to be produced and accumulated in the fermentation medium; and
  (b) collecting the L-amino acid from the fermentation medium.

79. The process of claim 78, wherein the L-amino acid is L-lysine or L-threonine.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 2147 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 584..1930

(xi) SEQUENCE DESCRIPTION: SEQ ID NO:1:

```
TCGAAGTGTT TCTGTAGTGC CTGCCAGGCA GCGGTCTGCG TTGGATTGAT GTTTTTCATT        60

AGCAATACTC TTCTGATTTT GAGAATTGTG ACTTTGGAAG ATTGTAGCGC CAGTCACAGA       120

AAAATGTGAT GGTTTTAGTG CCGTTAGCGT AATGTTGAGT GTAAACCCTT AGCGCAGTGA       180

AGCATTTATT AGCTGAACTA CTGACCGCCA GGAGTGGATG AAAAATCCGC ATGACCCCAT       240

CGTTGACAAC CGCCCCGCTC ACCCTTTATT TATAAATGTA CTACCTGCGC TAGCGCAGGC       300

CAGAAGAGGC GCGTTGCCCA AGTAACGGTG TTGGAGGAGC CAGTCCTGTG ATAACACCTG       360

AGGGGGTGCA TCGCCGAGGT GATTGAACGG CTGGCCACGT TCATCATCGG CTAAGGGGGC       420

TGAATCCCCT GGGTTGTCAC CAGAAGCGTT CGCAGTCGGG CGTTTCGCAA GTGGTGGAGC       480

ACTTCTGGGT GAAAATAGTA GCGAAGTATC GCTCTGCGCC CACCCGTCTT CCGCTCTTCC       540

CTTGTGCCAA GGCTGAAAAT GGATCCCCTG ACACGAGGTA GTT ATG TCT GAA ATT        595
                                              Met Ser Glu Ile
                                                1

GTT GTC TCC AAA TTT GGC GGT ACC AGC GTA GCT GAT TTT GAC GCC ATG        643
Val Val Ser Lys Phe Gly Gly Thr Ser Val Ala Asp Phe Asp Ala Met
  5              10                  15                  20

AAC CGC AGC GCT GAT ATT GTG CTT TCT GAT GCC AAC GTG CGT TTA GTT        691
Asn Arg Ser Ala Asp Ile Val Leu Ser Asp Ala Asn Val Arg Leu Val
                25                  30                  35

GTC CTC TCG GCT TCT GCT GGT ATC ACT AAT CTG CTG GTC GCT TTA GCT        739
Val Leu Ser Ala Ser Ala Gly Ile Thr Asn Leu Leu Val Ala Leu Ala
            40                  45                  50

GAA GGA CTG GAA CCT GGC GAG CGA TTC GAA AAA CTC GAC GCT ATC CGC        787
Glu Gly Leu Glu Pro Gly Glu Arg Phe Glu Lys Leu Asp Ala Ile Arg
        55                  60                  65

AAC ATC CAG TTT GCC ATT CTG GAA CGT CTG CGT TAC CCG AAC GTT ATC        835
Asn Ile Gln Phe Ala Ile Leu Glu Arg Leu Arg Tyr Pro Asn Val Ile
    70                  75                  80

CGT GAA GAG ATT GAA CGT CTG CTG GAG AAC ATT ACT GTT CTG GCA GAA        883
Arg Glu Glu Ile Glu Arg Leu Leu Glu Asn Ile Thr Val Leu Ala Glu
 85                  90                  95                 100

GCG GCG GCG CTG GCA ACG TCT CCG GCG CTG ACA GAT GAG CTG GTC AGC        931
Ala Ala Ala Leu Ala Thr Ser Pro Ala Leu Thr Asp Glu Leu Val Ser
                105                 110                 115
```

-continued

| | |
|---|---|
| CAC GGC GAG CTG ATG TCG ACC CTG CTG TTT GTT GAG ATC CTG CGC GAA<br>His Gly Glu Leu Met Ser Thr Leu Leu Phe Val Glu Ile Leu Arg Glu<br>             120                           125                    130 | 979 |
| CGC GAT GTT CAG GCA CAG TGG TTT GAT GTA CGT AAA GTG ATG CGT ACC<br>Arg Asp Val Gln Ala Gln Trp Phe Asp Val Arg Lys Val Met Arg Thr<br>             135                           140                    145 | 1027 |
| AAC GAC CGA TTT GGT CGT GCA GAG CCA GAT ATA GCC GCG CTG GCG GAA<br>Asn Asp Arg Phe Gly Arg Ala Glu Pro Asp Ile Ala Ala Leu Ala Glu<br>   150                          155                           160 | 1075 |
| CTG GCC GCG CTG CAG CTG CTC CCA CGT CTC AAT GAA GGC TTA GTG ATC<br>Leu Ala Ala Leu Gln Leu Leu Pro Arg Leu Asn Glu Gly Leu Val Ile<br>165                     170                         175                         180 | 1123 |
| ACC CAG GGA TTT ATC GGT AGC GAA AAT AAA GGT CGT ACA ACG ACG CTT<br>Thr Gln Gly Phe Ile Gly Ser Glu Asn Lys Gly Arg Thr Thr Thr Leu<br>                    185                         190                         195 | 1171 |
| GGC CGT GGA GGC AGC GAT TAT ACG GCA GCC TTG CTG GCG GAG GCT TTA<br>Gly Arg Gly Gly Ser Asp Tyr Thr Ala Ala Leu Leu Ala Glu Ala Leu<br>             200                           205                    210 | 1219 |
| CAC GCA TCT CGT GTT GAT ATC TGG ACC GAC GTC CCG GGC ATC TAC ACC<br>His Ala Ser Arg Val Asp Ile Trp Thr Asp Val Pro Gly Ile Tyr Thr<br>                    215                         220                    225 | 1267 |
| ACC GAT CCA CGC GTA GTT TCC GCA GCA AAA CGC ATT GAT GAA ATC GCG<br>Thr Asp Pro Arg Val Val Ser Ala Ala Lys Arg Ile Asp Glu Ile Ala<br>230                     235                         240 | 1315 |
| TTT GCC GAA GCG GCA GAG ATG GCA ACT TTT GGT GCA AAA GTA CTG CAT<br>Phe Ala Glu Ala Ala Glu Met Ala Thr Phe Gly Ala Lys Val Leu His<br>245                     250                       255                    260 | 1363 |
| CCG GCA ACG TTG CTA CCC GCA GTA CGC AGC GAT ATC CCG GTC TTT GTC<br>Pro Ala Thr Leu Leu Pro Ala Val Arg Ser Asp Ile Pro Val Phe Val<br>                    265                         270                    275 | 1411 |
| GGC TCC AGC AAA GAC CCA CGC GCA GGT GGT ACG CTG GTG TGC AAT AAA<br>Gly Ser Ser Lys Asp Pro Arg Ala Gly Gly Thr Leu Val Cys Asn Lys<br>             280                           285                    290 | 1459 |
| ACT GAA AAT CCG CCG CTG TTC CGC GCT CTG GCG CTT CGT CGC AAT CAG<br>Thr Glu Asn Pro Pro Leu Phe Arg Ala Leu Ala Leu Arg Arg Asn Gln<br>                    295                         300                    305 | 1507 |
| ACT CTG CTC ACT TTG CAC AGC CTG AAT ATG CTG CAT TCT CGC GGT TTC<br>Thr Leu Leu Thr Leu His Ser Leu Asn Met Leu His Ser Arg Gly Phe<br>310                     315                         320 | 1555 |
| CTC GCG GAA GTT TTC GGC ATC CTC GCG CGG CAT AAT ATT TCG GTA GAC<br>Leu Ala Glu Val Phe Gly Ile Leu Ala Arg His Asn Ile Ser Val Asp<br>325                     330                       335                    340 | 1603 |
| TTA ATC ACC ACG TCA GAA GTG AGC GTG GCA TTA ACC CTT GAT ACC ACC<br>Leu Ile Thr Thr Ser Glu Val Ser Val Ala Leu Thr Leu Asp Thr Thr<br>                        345                         350                    355 | 1651 |
| GGT TCA ACC TCC ACT GGC GAT ACG TTG CTG ACG CAA TCT CTG CTG ATG<br>Gly Ser Thr Ser Thr Gly Asp Thr Leu Leu Thr Gln Ser Leu Leu Met<br>             360                           365                    370 | 1699 |
| GAG CTT TCC GCA CTG TGT CGG GTG GAG GTG GAA GAA GGT CTG GCG CTG<br>Glu Leu Ser Ala Leu Cys Arg Val Glu Val Glu Glu Gly Leu Ala Leu<br>                    375                         380                    385 | 1747 |
| GTC GCG TTG ATT GGC AAT GAC CTG TCA AAA GCC TGC GGC GTT GGC AAA<br>Val Ala Leu Ile Gly Asn Asp Leu Ser Lys Ala Cys Gly Val Gly Lys<br>             390                           395                    400 | 1795 |
| GAG GTA TTC GGC GTA CTG GAA CCG TTC AAC ATT CGC ATG ATT TGT TAT<br>Glu Val Phe Gly Val Leu Glu Pro Phe Asn Ile Arg Met Ile Cys Tyr<br>405                     410                       415                    420 | 1843 |
| GGC GCA TCC AGC CAT AAC CTG TGC TTC CTG GTG CCC GGC GAA GAT GCC<br>Gly Ala Ser Ser His Asn Leu Cys Phe Leu Val Pro Gly Glu Asp Ala<br>                    425                         430                    435 | 1891 |

-continued

```
GAG CAG GTG GTG CAA AAA CTG CAT AGT AAT TTG TTT GAG TAAATACTGT      1940
Glu Gln Val Val Gln Lys Leu His Ser Asn Leu Phe Glu
            440                 445

ATGGCCTGGA AGCTATATTT CGGGCCGTAT TGATTTTCTT GTCACTATGC TCATCAATAA   2000

ACGAGCCTGT ACTCTGTTAA CCAGCGTCTT TATCGGAGAA TAATTGCCTT TAATTTTTTT   2060

ATCTGCATCT CTAATTAATT ATCGAAAGAG ATAAATAGTT AAGAGAAGGC AAAATGAATA   2120

TTATCAGTTC TGCTCGCAAA GGAATTC                                      2147
```

(2) INFORMATION FOR SEQ ID NO:2:

(i) SEQUENCE CHARACTERISTICS:
        (A) LENGTH: 449 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Glu Ile Val Val Ser Lys Phe Gly Gly Thr Ser Val Ala Asp
  1               5                  10                  15

Phe Asp Ala Met Asn Arg Ser Ala Asp Ile Val Leu Ser Asp Ala Asn
                 20                  25                  30

Val Arg Leu Val Val Leu Ser Ala Ser Ala Gly Ile Thr Asn Leu Leu
             35                  40                  45

Val Ala Leu Ala Glu Gly Leu Glu Pro Gly Glu Arg Phe Glu Lys Leu
         50                  55                  60

Asp Ala Ile Arg Asn Ile Gln Phe Ala Ile Leu Glu Arg Leu Arg Tyr
     65                  70                  75                  80

Pro Asn Val Ile Arg Glu Ile Glu Arg Leu Leu Glu Asn Ile Thr
                 85                  90                  95

Val Leu Ala Glu Ala Ala Ala Leu Ala Thr Ser Pro Ala Leu Thr Asp
                100                 105                 110

Glu Leu Val Ser His Gly Glu Leu Met Ser Thr Leu Leu Phe Val Glu
                115                 120                 125

Ile Leu Arg Glu Arg Asp Val Gln Ala Gln Trp Phe Asp Val Arg Lys
        130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
                180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
    210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
                260                 265                 270

Pro Val Phe Val Gly Ser Ser Lys Asp Pro Arg Ala Gly Gly Thr Leu
            275                 280                 285

Val Cys Asn Lys Thr Glu Asn Pro Pro Leu Phe Arg Ala Leu Ala Leu
        290                 295                 300
```

```
Arg Arg Asn Gln Thr Leu Leu Thr Leu His Ser Leu Asn Met Leu His
305                 310                 315                 320

Ser Arg Gly Phe Leu Ala Glu Val Phe Gly Ile Leu Ala Arg His Asn
            325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
            355                 360                 365

Ser Leu Leu Met Glu Leu Ser Ala Leu Cys Arg Val Glu Val Glu Glu
        370                 375                 380

Gly Leu Ala Leu Val Ala Leu Ile Gly Asn Asp Leu Ser Lys Ala Cys
385                 390                 395                 400

Gly Val Gly Lys Glu Val Phe Gly Val Leu Glu Pro Phe Asn Ile Arg
            405                 410                 415

Met Ile Cys Tyr Gly Ala Ser Ser His Asn Leu Cys Phe Leu Val Pro
            420                 425                 430

Gly Glu Asp Ala Glu Gln Val Val Gln Lys Leu His Ser Asn Leu Phe
            435                 440                 445

Glu
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:3:

CTTCCCTTGT GCCAAGGCTG								20

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:4:

GAATTCCTTT GCGAGCAG								18

(2) INFORMATION FOR SEQ ID NO:5:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC DNA"

(xi) SEQUENCE DESCRIPTION: SEQ ID NO:5:

GAGGTCAGAC CGGTGGTATC AAGGGTTAAT GC								32

(2) INFORMATION FOR SEQ ID NO:6:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "SYNTHETIC DNA"

(xi) SEQUENCE DESCRIPTION: SEQ ID NO:6:

GGTATCAAGG GTTAATGCCA CGCTCACTTC GATCGTGGTG ATTAAGTCTA C          51

(2) INFORMATION FOR SEQ ID NO:7:

(i) SEQUENCE CHARACTERISTICS:
    (A) LENGTH: 51 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "SYNTHETIC DNA"

(xi) SEQUENCE DESCRIPTION: SEQ ID NO:7:

GGTATCAAGG GTTAATGCCA CGCTCACTTC AACCGTGGTG ATTAAGTCTA C          51

(2) INFORMATION FOR SEQ ID NO:8:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "SYNTHETIC DNA"

(xi) SEQUENCE DESCRIPTION: SEQ ID NO:8:

TGCAGTATAT TCAGGCTGTG CAAAGTGAGC                                  30